US007576226B2

(12) United States Patent
Tuba et al.

(10) Patent No.: US 7,576,226 B2
(45) Date of Patent: Aug. 18, 2009

(54) PROCESS OF MAKING ISOMERS OF NORELGESTROMIN AND METHODS USING THE SAME

(75) Inventors: Zoltán Tuba, Budapest (HU); Sándor Mahó, Budapest (HU); György Keserü, Telki (HU); József Kozma, Budapest (HU); János Horváth, Budapest (HU); Gábor Balogh, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 895 days.

(21) Appl. No.: 10/879,710

(22) Filed: Jun. 30, 2004

(65) Prior Publication Data

US 2005/0032764 A1 Feb. 10, 2005

(30) Foreign Application Priority Data

Jun. 30, 2003 (HU) .................................. 0301981
Jun. 30, 2003 (HU) .................................. 0301982

(51) Int. Cl.
*C07J 41/00* (2006.01)
(52) U.S. Cl. .................................... 552/520
(58) Field of Classification Search ................... 552/520
See application file for complete search history.

(56) References Cited

U.S. PATENT DOCUMENTS

| 2,774,777 | A | 12/1956 | Djerassi et al. |
| 3,437,674 | A | 4/1969 | Shroff |
| 3,532,689 | A | 10/1970 | Shroff |
| 3,545,397 | A | 12/1970 | Andrews |
| 3,629,415 | A | 12/1971 | Shroff |
| 3,761,496 | A | 9/1973 | Tuba et al. |
| 3,780,073 | A | 12/1973 | Shroff |
| 3,912,768 | A | 10/1975 | Gardi et al. |
| RE28,690 | E | 1/1976 | Lehmann et al. |
| 3,959,322 | A | 5/1976 | Hughes et al. |
| 3,975,412 | A | 8/1976 | Stein |
| 4,012,496 | A | 3/1977 | Schöpflin et al. |
| 4,027,019 | A | 5/1977 | Shroff |
| 4,144,254 | A | 3/1979 | Imai et al. |
| 4,186,128 | A | 1/1980 | Warnant et al. |
| 4,292,965 | A | 10/1981 | Nash et al. |
| 4,368,160 | A | 1/1983 | Boór nee Mezei et al. |
| 4,871,543 | A | 10/1989 | Lindskog et al. |
| 4,906,169 | A | 3/1990 | Chien et al. |
| 4,906,463 | A | 3/1990 | Cleary et al. |
| 4,973,468 | A | 11/1990 | Chiang et al. |
| 5,006,342 | A | 4/1991 | Cleary et al. |
| 5,059,426 | A | 10/1991 | Chiang et al. |
| 5,188,835 | A | 2/1993 | Lindskog et al. |
| 5,252,334 | A | 10/1993 | Chiang et al. |
| 5,422,119 | A | 6/1995 | Casper |
| 5,474,783 | A | 12/1995 | Miranda et al. |
| 5,656,286 | A | 8/1997 | Miranda et al. |
| 5,876,746 | A | 3/1999 | Jona et al. |
| 5,958,446 | A | 9/1999 | Miranda et al. |
| 5,972,377 | A | 10/1999 | Jona et al. |
| 6,024,976 | A | 2/2000 | Miranda et al. |
| 6,071,531 | A | 6/2000 | Jona et al. |
| 7,345,183 | B2 | 3/2008 | Tombari et al. |
| 7,393,964 | B2 | 7/2008 | Farnesi et al. |
| 2003/0219471 | A1 | 11/2003 | Caubel et al. |
| 2003/0225047 | A1 | 12/2003 | Caubel et al. |
| 2003/0225048 | A1 | 12/2003 | Caubel et al. |
| 2003/0229057 | A1 | 12/2003 | Caubel et al. |
| 2004/0043171 | A1 | 3/2004 | Audett |
| 2004/0266741 | A1 | 12/2004 | Tombari et al. |
| 2006/0035872 | A1 | 2/2006 | Villa et al. |

FOREIGN PATENT DOCUMENTS

| AT | 348 151 B | 2/1979 |
| CA | 1122592 | 4/1982 |
| CH | 494 218 | 7/1970 |

(Continued)

OTHER PUBLICATIONS

Abrams, L.S., et al., "Pharmacokinetics of Norelgestromin and Ethinyl Estradiol from Two Consecutive Contraceptive Patches," *J. Clin. Pharmacol.* 41:1232-1237 American College of Clinical Pharmacology (2001).

Aicher, T.D., et al., "Triterpene and Diterpene Inhibitors of Pyruvate Dehydrogenase Kinase (PDK)," *Bioorganic Med. Chem. Letters*, 9:2223-2228 Elsevier Science Ltd. (1999).

Bringer, J., "Norgestimate: A clinical overview of a new progestin," *Am. J. Obstet. Gynecol.* 166: 1969-1977 Mosby-Year Book, Inc. (1992).

Ferenczi-Fodor, K., et al., "Separation and determination of steroid isomers on amino-bonded silica by conventional and overpressurized thin-layer chromatography," *J. Chromat.* 392: 464-469, Elsevier Science Publishers B.V. (1987).

Gazdag, M., et al., "Separation of Isomeric Compounds as Cyclodextrin Inclusion Complexes on a Cyanopropylsilica Stationary Phase," *J. Chromat.* 371:227-234 Elsevier Science Publishers B.V. (1986).

(Continued)

*Primary Examiner*—Barbara P Badio
(74) *Attorney, Agent, or Firm*—Sterne, Kessler, Goldstein & Fox P.L.L.C.

(57) ABSTRACT

The invention is directed to a process of preparing substantially pure d-(17α)-13-ethyl-17-hydroxy-18,19-dinorpregn-4-ene-20-yn-3-one-3E- and -3Z-oxime isomers, as well as a process for the synthesis of the mixture of isomers and the pure isomers. The invention also relates to substantially pure d-(17α)-13-ethyl-17-hydroxy-18,19-dinorpregn-4-ene20-yn-3-one-3E-oxime and substantially pure d-(17α)-13-ethyl-17-hydroxy-18,19-dinorpregn-4-ene-20-yn-3-one-3Z-oxime isomer. Further aspects of the invention include a composition comprising substantially pure d-(17α)-13-ethyl-17-hydroxy-18,19-dinorpregn-4-ene20-yn-3-one-3E-oxime or substantially pure d-(17α)-13-ethyl-17-hydroxy-18,19-dinorpregn-4-ene-20-yn-3-one-3Z-oxime isomer, and methods of treatment using said compositions.

20 Claims, 1 Drawing Sheet

FOREIGN PATENT DOCUMENTS

Figure 1:
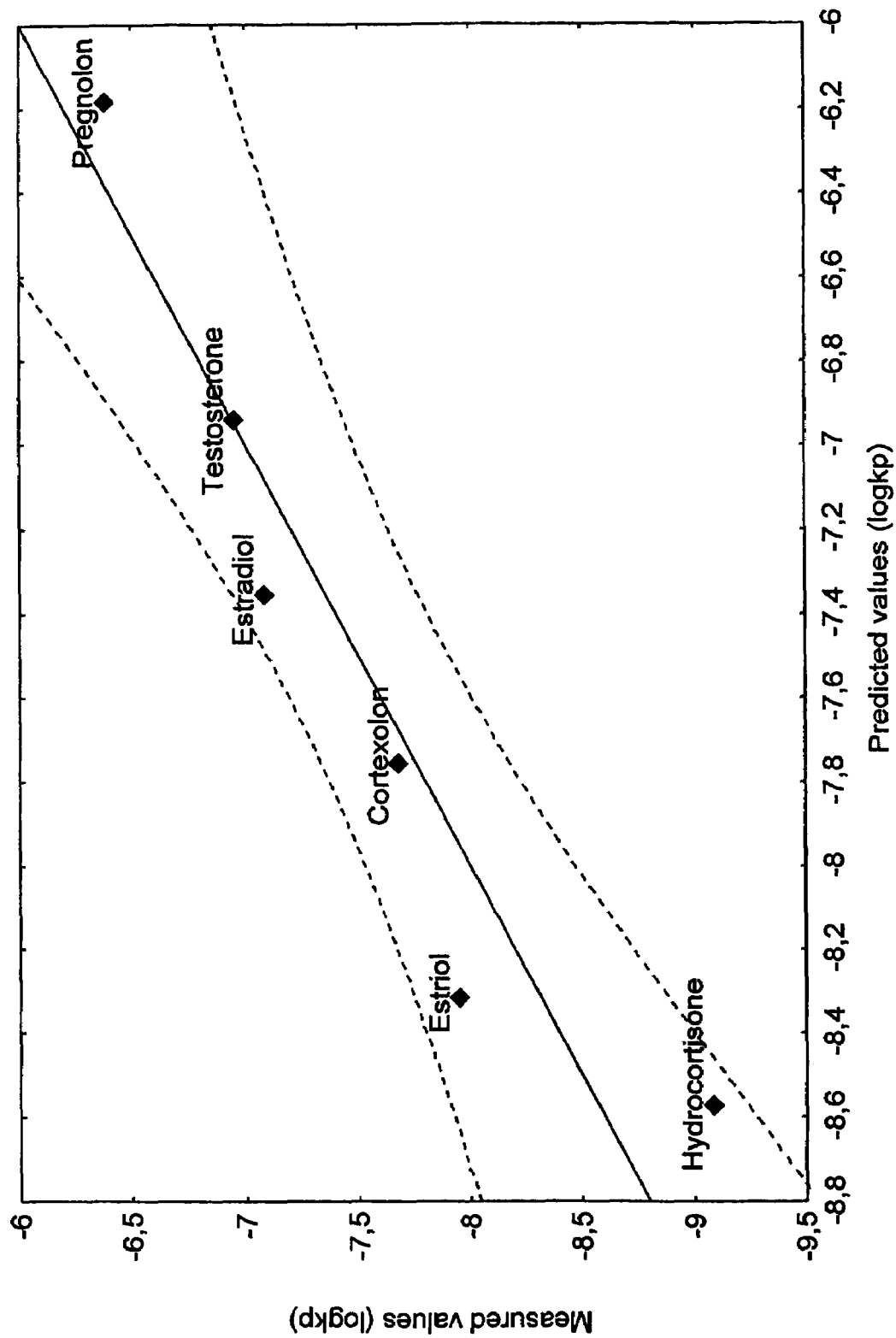

| | | |
|---|---|---|
| DE | 136502 | 7/1979 |
| EP | 0 063 369 | 10/1982 |
| EP | 0 309 263 | 3/1989 |
| GB | 1123104 | 8/1968 |
| GB | 1 452 179 | 10/1976 |
| WO | WO 96/40087 | 12/1996 |
| WO | WO 96/40355 | 12/1996 |
| WO | WO 2005/000867 | 1/2005 |
| WO | WO 2005/000868 | 1/2005 |

OTHER PUBLICATIONS

Hara, S., and Kitaro, O., "Synthesis and Characters of 1-Substituted A-Norsteroids," *Tetrahedron Letters 10*:1057-1061 Pergamon Press Ltd. (1966).

Hara, S., et al., "Quantitative Resolution of *Syn* and *Anti* Isomers of Steroidal α, β-Unsaturated Oximes and *O*-methyloximes," *Chemistry & Industry 1*:832-833 (1967).

Herz, S., et al., "Esterification of Acid Chlorides with Thallium and Potassium Salts of 19-Norethisterone: Formation of 17-Enol Esters," *Steroids 40*:261-266 Holden-Day, Inc. (1982).

Leung, S.L., et al., "Norethisterone and Levonorgestrel Esters: A Novel Synthetic Method," *Steroids 46*:639-647 Holden-Day, Inc. (1985).

McGuire, J.L., et al., "Pharmacologic and pharmacokinetic characteristics of norgestimate and its metabolites," *Am. J. Obstet. Gynecol. 163*:2127-2131 Mosby-Year Book, Inc. (1990).

Pasqualini, J.R., et al., "Norelgestromin as selective estrogen enzyme modulator in human breast cancer cell lines. Effect on sulfatase activity in comparison to medroxyprogesterone acetate," *J. Steroid Biochem. & Mol. Biol. 84*:193-198 Elsevier Science Ltd. (Feb. 2003).

Patthy, M., and Tomori, E., "High-Performance Liquid Chromatography and Gas-Liquid Chromatography of Some Norgestrel Intermediates. Physical Properties of Isolated *SYN*- and *ANTI*- Isomers of Oximes," *J. Chromat. 191*:145-154 Elsevier Scientific Publishing Company (1980).

Petersen, R.V., et al., "Controlled Release of Progestins From poly(α-Amino Acid) Carriers," *Controlled Release Bioactive Materials* :45-60 Academic Press (1980).

Quinkert, G., et al., eds. "(-)-Norgestrel," *Synform 3*:19-32, VCH Verlagsgesellschaft (1985).

Shroff, A.P., et al., "Synthesis and Antifertility Activity of Some Oximinoandrostenes," *J. Med. Chem. 16*:113-115 American Chemical Society (1973).

Szentesi, A., et al., "Determination of Circular Dichroism and Ultraviolet Spectral Parameters of Norgestimate- and Other $\Delta^4$-3-Ketosteroid Oxime Isomers Via Normal Phase HPLC Method," *Curr. Med. Chem. 8*:1341-1347 Bentham Science Publishers Ltd. (2001).

Ortho-McNeil Pharmaceutical, inc., "Ortho Evra™ (Norelgestromin/Ethinyl Estradiol Transdermal System)," Product Information, Ortho-McNeil Pharmaceutical, Inc., Raritan, NJ., 8 pages (2001).

Ortho-McNeil Pharmaceutical, inc., "Ortho Tri-Cyclen® Tablets, Ortho-Cyclen® Tablets (norgestimate/ethinyl estradiol)," Product Information, Ortho-McNeil Pharmaceutical, Inc., Raritan, NJ., 6 pages (2001).

Derwent English language abstract, Accession No. 1979-70047B, for DD 136502 (Document AN1).

STNEasy Database, Accession No. 1982:582735, English language abstract for CA1122592 (Document AO1).

Co-pending U.S. Appl. No. 10/879,708, inventors Tuba, Z., et al., file Jun. 30, 2004 (Not Published).

Rufer, C., et al., "Totalsynthese von optisch aktiven 13-Äthyl-gonan-Derivaten," *Liebigs Annalen der Chemie 702*:141-148, (Verlag Chemie, Germany) (1967), English Abstract Only.

Sisenwine, S.F., et al., "The Conversion of *d*-Norgestrel-3-Oxime-17-Acetate to *d*-Norgestel in Female Rhesus Monkeys," *Contraception 15*:25-37, (Geron-X, Inc., Los Altos, CA) (1977).

Derwent World Patent Index, Dialog File 351, English Language Abstract for Swiss Patent No. CH 494 218 (Document AM2), Accession No. 532761, 1970.

Derwent World Patent Index, Dialog File 351, English Language Abstract for Austrian Patent No. AT 348 151 (Document AO2), Accession No. 1001052, 1979.

STNEasy from CAplus, Accession No. 1967:105091, English Language Abstract of: Rufer, C., et al., "Totalsynthese von optisch akiven 13-Äthyl-gonan-Derivaten," *Liebigs Annalen der Chemie 702*:141-148, Verlag Chemie (1967) (Document AS8).

International Search Report for International Patent Application No. PCT/HU2004/000030, mailed Oct. 15, 2004, European Patent Office, Rijswijk, Netherlands.

Written Opinion of the International Searching Authority for International Patent Application No. PCT/HU2004/000030, mailed Oct. 15, 2004, European Patent Office, Munich, Germany.

International Search Report for International Patent Application No. PCT/HU2004/000031, mailed Oct. 11, 2004, European Patent Office, Rijswijk, Netherlands.

Derwent WPI, Dialog File No. 351, Accession No. 3545094, English language abstract for European Patent No. EP 0 063 369 (Document AO3), 1982.

PROCESS OF MAKING ISOMERS OF NORELGESTROMIN AND METHODS USING THE SAME

CROSS REFERENCE TO RELATED APPLICATIONS

Priority under 35 U.S.C. § 119(a)-(d) is hereby claimed to Hungarian patent application No. P 03 01981, filed Jun. 30, 2003, and to Hungarian patent application No. P 03 01982, filed Jun. 30, 2003, both of which are incorporated by reference in their entireties.

BACKGROUND OF THE INVENTION

The present invention relates to a process for producing norelgestromin, including the oxime isomers thereof, and suitable compositions comprising norelgestromin. The invention is also directed to methods of treatment comprising administering norelgestromin.

Background Art

The synthesis and biological investigation of 3-oximino-androstene- and gonene derivatives containing a sterane skeleton started in the 1960s. The application of dl-(17α)-13-ethyl-17-(acetyloxy)-18,19-dinorpregn-4-ene-20-yn-3-one-oxime derivatives as postcoital contraceptives is suggested in U.S. Pat. No. 3,780,073.

The synthesis of dl- and d-(17α)-13-ethyl-17-hydroxy-18,19-dinorpregn-4-ene-20-yn-3-one-oxime is described in Hungarian Patent No. 165,356. The compounds are described as the intermediates of the synthesis of the racemic and optically active norgestrel, but their biological activity is not given.

The synthesis of d-(17α)-13-ethyl-17-(acetyloxy)-18,19-dinorpregn-4-ene-20-yn-3-one-oxime (norgestimate) is described in the U.S. Pat. No. 4,027,019.

The biological and clinical investigation of norgestimate demonstrated advantageous inhibition of fertility. Norgestimate in combination with ethinyl estradiol gained therapeutic application as ORTHO-CYCLEN® and CILEST. The use of the optically active isomer of norgestimate made possible the application of the active ingredient in lower dosage than in the case of the racemic mixture Progress occurred with the synthesis of 17-deacetylnorgestimate (norelgestromin) and the pharmacological as well as clinical investigation thereof. The following publications, *Am. J. Obstet. Gynecol.*, 166, 1969-77 (1992) and *Am. J. Obstet. Gynecol*, 163:2127-31 (1990), disclose that the metabolites of orally applied norgestimate are 17-deacetyl-norgestimate and 3-keto-norgestimate (d-norgestrel acetate), as well as d-norgestrel (levonorgestrel), which have significant biological activity.

U.S. Pat. No. 4,906,169 describes the use of norgestimate and d-norgestrel in combination with an estrogen component in transdermal patch.

Published PCT application WO 96/40355 discloses the use of deacetylnorgestimate, one of the metabolites of norgestimate, alone or in combination with an estrogen component in a transdermal patch.

BRIEF SUMMARY OF THE INVENTION

It is generally desirable to decrease the dose of active ingredients used in the therapy. This is especially true for steroid derivatives possessing high biological activity. The aim of our research was to synthesize and investigate the biological effect of the pure optical antipodes of steroid derivatives, which had been described in the literature earlier as racemic mixtures.

The invention relates to a process of preparing substantially pure d-(17α)-13-ethyl-17-hydroxy-18,19-dinorpregn-4-ene-20-yn-3-one-3E-oxime of Formula I

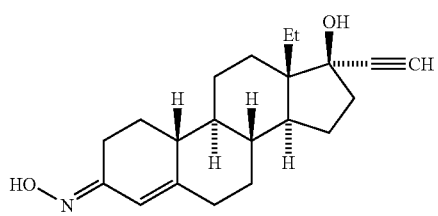

The invention also relates to a process of preparing substantially pure d-(17α)-13-ethyl-17-hydroxy-18,19-dinorpregn-4-ene-20-yn-3-one-3Z-oxime of Formula II

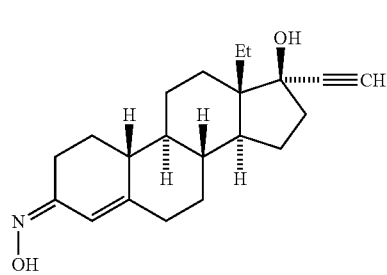

The invention also relates to the process for the synthesis of the mixture of the above isomers and of the pure isomers. The invention also relates to compositions (such as pharmaceutical compositions) comprising a substantially pure oxime of Formula I or II. In another embodiment, the present invention is directed to an isolated, substantially pure compound of Formula I. In another embodiment, the invention is directed to an isolated, substantially pure compound of Formula II. The isolated compounds are preferably suitable for use in a pharmaceutical composition. In other embodiments, the composition of the present invention further comprises other active ingredients (for example, an estrogen agent) together with pharmaceutical auxiliary materials commonly used in practice and as described herein. In yet other embodiments, the present invention is directed to methods of treatment comprising administering compounds and compositions of the present invention. The compositions of the present invention are useful for treating a number of conditions, including hormone replacement therapy. Furthermore, the compounds and compositions are useful in the preparation of and use as contraceptive agents. Another aspect of the invention is a process of synthesizing norelgestromin and the oxime isomers thereof on an industrial scale.

It is believed that the method of the present invention differs from prior art methods of preparing compounds of Formula I or II. In certain embodiments, the present invention prepares a compound of Formula I or II having a higher purity with respect to the oxime isomer.

BRIEF DESCRIPTION OF THE DRAWINGS/FIGURES

FIG. 1 shows the correlation between measured and predicted logkp data (95% confidence intervals are indicated by dashed lines) for six steroid-type compounds.

DETAILED DESCRIPTION OF THE INVENTION

The separation of several known steroids, among them norelgestromin, by high pressure chromatography is described in: *J. Chromatogr.*, 392:464-9 (1987), but only the chromatographical parameters and not the physicochemical properties of the separated oxime isomers, which prove the structures, are given. Furthermore, the isomers in isolated, substantially pure form are not described.

The examination of some intermediate of the synthesis of norgestrel by high performance liquid chromatography (HPLC) and gas-liquid chromatography (GLC) is described in *J. Chromatogr.* 191(1):145-54. (1980). Among the above compounds are the racemic mixture and the optically pure oxime derivatives as well, which are disclosed in the Hungarian Patent No. 165,356. From the description, it is ambiguous whether the optically pure or the racemic mixture of steroid oxime derivatives were examined. According to the above publication, the oxime isomers were separated by normal phase analytical HPLC, and their structures were elucidated. For the structure elucidation, they refer to the publication of Hara and coworkers (*Chem. Ind.* (*London*), 832 (1967)), where the syn and anti oxime isomers of testosterone were separated. Their structures were examined by NMR and UV spectroscopical methods. The significant difference measured in the molar absorption of the two oxime isomers at 242 nm wavelength was emphasized.

A general goal of the pharmaceutical industry is the synthesis of structurally homogeneous and stereochemically pure active ingredients (i.e., single enantiomer and diastereomer), and their use in therapy, which may lead to the application of a lower dose of the active ingredients having unambiguous biological activity profile and therefore decreased side effects.

As described above, the known procedures for the synthesis of steroid compounds containing an oxime group at position 3, e.g., norgestimate and 17-deacetylnorgestimate, lead to an isomeric mixture of oximes, where the ratio of isomers is about 60:40 to about 64:36 E/Z-oximes.

Surprisingly, it was found by the present inventors that using the process according to invention described herein for the oximation reaction, and for the work-up procedure of the obtained mixture of oximes, either the d-(17α)-13-ethyl-17-hydroxy-18,19-dinorpregn-4-ene-20-yn-3-one-(3E)-oxime or d-(17α)-13-ethyl-17-hydroxy-18,19-dinorpregn-4-ene-20-yn-3-one-(3E)-oxime, as well as the mixture of 3E- and 3Z-oximes, can be synthesized and prepared as required.

In one embodiment, the invention relates to a process of preparing substantially pure d-(17α)-13-ethyl-17-hydroxy-18,19-dinorpregn-4-ene-20-yn-3-one-3E-oxime isomer of Formula I

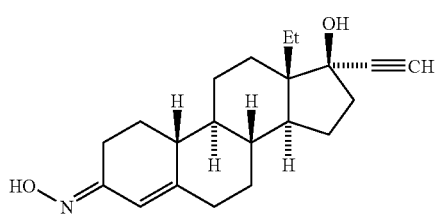

In another embodiment, the invention also relates to a process of preparing substantially pure d-(17α)-13-ethyl-17-hydroxy-18,19-dinorpregn-4-ene-20-yn-3-one-3Z-oxime isomer of Formula II

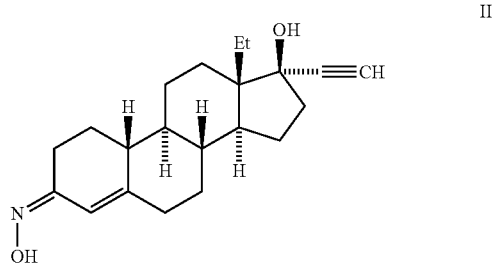

In addition, the invention relates to a process for the synthesis of the mixture of the above isomers and of the pure isomers. The invention also relates to compositions (such as pharmaceutical compositions) comprising a substantially pure oxime of Formulas I or II. In one embodiment, the present invention is directed to an isolated, substantially pure compound of Formula I. In another embodiment, the invention is directed to an isolated, substantially pure compound of Formula II. The isolated compounds are preferably suitable for use in a pharmaceutical composition. In other embodiments, the composition of the present invention further comprises other active ingredients (for example, an estrogen agent) together with pharmaceutical auxiliary materials commonly used in practice and as described herein.

In yet other embodiments, the present invention is directed to methods of treatment comprising administering compounds and compositions of the present invention. The compositions of the present invention are useful for treating a number of conditions, including hormone replacement therapy. Furthermore, the compounds and compositions are useful in the preparation of and use as contraceptive agents.

D-(17α)-13-ethyl-17-hydroxy-18,19-dinorpregn-4-ene-20-yn-3-one-oxime is used in therapy as a stereochemical mixture of isomers of E/Z oximes. The use of a single substantially pure isomer makes possible a number of advantages, including an increase in the homogeneity of the biological activity profile of a pharmaceutical composition comprising the isomer. Furthermore, the use of a substantially pure isomer allows one to take advantage of the different physical properties (for example solubility, permeability, absorption) of the individual isomer in realization of a more suitable application method in therapy.

Synthesis

In one embodiment, the process of preparing d-(17α)-13-ethyl-17-hydroxy-18,19-dinorpregn-4-ene-20-yn-3-one-(3E)-oxime comprises converting d-norgestrel into a mixture of norelgestromin oxime isomers; adding about 10 to about 25 volume percent of water to the reaction mixture comprising the norelgestromin isomers; and stirring the resulting mixture for at least about 24 hours. The process optionally comprises additional steps, such as adding additional water after the stirring period to precipitate the E-norelgestromin, and optionally further purifying the E-norelgestromin obtained from the process.

The d-norgestrel can be converted into norelgestromin under a variety of oximation conditions. For example, hydroxylammonium acetate or a hydroxylammonium salt can be used to convert d-norgestrel to norelgestromin. A suitable hydroxylammonium salt includes hydroxylammonium chloride. In certain embodiments, when a hydroxylammonium salt is used, a base is also use, such as for example acetate, pyridine, and the like. Of course, other procedures for forming the oxime group on norelgestromin are understood to be encompassed by the present invention. For example, any of the processes of oximation described in copending application Ser. No. 10/879,708 titled "Process for the synthesis of high purity d (17α)-13-ethyl-17-hydroxy-18,19-dinorpregn-4-ene-20-yn-3-one-oxime," filed Jun. 30, 2004, which is incorporated herein by reference in its entirety, can be used.

Additionally, any solvent or mixtures of solvents that allow the reaction to proceed as described can be used in each of the steps of the present invention. Both organic and inorganic solvents are known in the art. Such solvents include chloroform, dichloromethane, methanol, ethanol, ethyl acetate, acetone, benzene, toluene, carbon tetrachloride, acetic acid, tetrahydrofuran, and the like.

The precise temperature at which the reaction mixture is stirred, after addition of the water, can vary. In certain embodiments, the reaction mixture is stirred at a temperature of about 10° C. to about 30° C. In another embodiment, the reaction mixture is stirred at a temperature of about 0° C. to about 45° C. Generally, stirring at room temperature is suitable.

The resulting E-norelgestromin can be isolated using standard procedures, such as adding water to the reaction mixture, and isolating the precipitated product. Optionally, the E-norelgestromin is further purified by recrystallization in a suitable solvent.

In other embodiments, the step of converting d-norgestrel to norelgestromin is performed under an inert atmosphere. A suitable inert atmosphere includes but is not limited to nitrogen and argon. In certain embodiments, the inert atmosphere is a dry atmosphere having a low moisture content. Such inert atmospheres are understood in the art.

By way of example, the process according to this embodiment comprises converting d-norgestrel into a mixture of norelgestromin isomers; and adding to the reaction mixture about 10 to about 25 volume percent of water; and stirring the resulting mixture for at least 24 hours. In other embodiments, said d-norgestrel is reacted with hydroxylammonium acetate in a ratio of about 1.2 mol to about 5 mol per mole of said d-norgestrel, in acetic acid containing not more than 50 mass percent of water; at a temperature of about 15° C. to about 50° C.; and stirred for about 15 minutes to about 45 minutes. In another embodiment, said reaction mixture is stirred for about 24 to about 72 hours after the addition of water.

In another embodiment, the d-norgestrel is reacted with a hydroxylammonium salt in a ratio of about 1.2 to about 5 mol per mole of d-norgestrel, and with an alkali metal acetate in a ratio of not more than 1 mole per mole of said hydroxylammonium salt; in acetic acid containing not more than 50 mass percent of water; at a temperature of about 15° C. to about 50° C.; and stirred for about 15 minutes to about 45 minutes.

In another embodiment of the invention, hydroxyammonium hydrochloride and sodium acetate are suspended in glacial acetic acid. The suspension is stirred, for example, for 1 hour, and the formed sodium chloride is filtered. Under nitrogen, d-norgestrel is added to the stirred solution, and stirring is continued until the reaction is complete. Then water is added to the reaction mixture, and stirring is continued for about 20 to about 100 hours, for example, for about 50 hours. The reaction mixture is poured into water. The precipitated product is isolated and washed, and then dried. The E-norelgestromin is then optionally recrystallized from a suitable solvent. Suitable solvents include, but are not necessarily limited to, acetonitrile and ethyl acetate.

Other suitable ratios of hydroxylammonium chloride to norgestrel include about 2:1, about 3:1, and about 4:1.

In another embodiment, the process of preparing d-(17α)-13-ethyl-17-hydroxy-18,19-dinorpregn-4-ene-20-yn-3-one-(3Z)-oxime comprises converting d-norgestrel into a mixture of norelgestromin oxime isomers; and after addition of about 10-fold volume of water, the precipitated isomeric mixture is isolated and stirred in dichloromethane. For example, in one embodiment the process of preparing d-(17α)-13-ethyl-17-hydroxy-18,19-dinorpregn-4-ene-20-yn-3-one-(3Z)-oxime comprises a method as described above; and, after addition of about 10-fold volume of water, the precipitated isomeric mixture is isolated and stirred in dichloromethane. The insoluble (3E)-oxime isomer of Formula I is filtered from the dichloromethane solution. The filtrate is purified, for example, by column chromatography, to give the (3Z)-oxime of Formula II. For example, the Z-norelegestromin can be purified by column chromatography using silica gel as adsorbent and a mixture of apolar-polar solvents as eluent. Optionally, the Z-norelgestromin is further purified by recrystallization in a suitable solvent.

The preceding embodiment is also suitable for the preparation of d-(17α)-13-ethyl-17-hydroxy-18,19-dinorpregn-4-ene-20-yn-3-one-(3E)-oxime. In this case, the insoluble (3E)-oxime isomer of Formula I is filtered from the dichloromethane solution. In one embodiment, the E-norelgestromin is obtained having a isomeric purity of at least 90%, preferably at least 94%. The E-oxime isomer so obtained can then be further purified, for example, by recrystallization.

By way of example, an embodiment of the invention comprises the following process. A suspension of sodium acetate, hydroxylammonium hydrochloride, and aqueous acetic acid is vigorously stirred, for example at room temperature for about 1 hour. The precipitated sodium chloride is filtered. D-norgestrel is added to the solution under an inert atmosphere, for example under nitrogen or argon, and the resulting mixture is stirred for about 0.5 hours to about 5 hours. Other suitable times include about 1, about 1.5, and about 2 hours. During this time, the temperature of the reaction is allowed to rise to about 45° C. When the reaction is complete, the reaction mixture is poured into water. The precipitated product is isolated and dried using standard techniques. For example, the isolated product is filtered, washed successively with water, 5% aqueous ammonium hydroxide solution, and then water until neutral, and then dried. The isolated product is a mixture of oxime isomers of norelgestromin, in certain embodiments having a ratio E:Z of about 60:40 to about 50:50. The mixture of isomers is then stirred in dichloromethane. The volume of dichloromethane may vary. Suitable volumes include 18-fold, 20-fold, and 22-fold volume. The time of stirring may vary as well. In one embodiment, the mixture is stirred for about 30 minutes. Other suitable times include but are not limited to 10, 20, 40, 50 and 60 minutes. In this way, the Z-oxime isomer is relatively soluble, whereas the E-oxime isomer of norelgestromin is less soluble and is filtered from the dichloromethane solution. The E-oxime norelgestromin obtained this way is in certain embodiments substantially pure. The E-isomer can optionally be dried, preferably below 60° C.

The mother liquor obtained after isolating the E-oxime isomer is then concentrated to yield a mixture of isomers, (e.g., Z oxime about 65%, E-oxime about 33%). The residue obtained is dissolved in dichloromethane and kept at a cooled temperature, for example about 0° C. to about 5° C. After some time, for example about 2 to about 8 hours, the precipitated crystalline product is filtered off, washed with dichloromethane, and dried to yield substantially pure Z-norelgestromin.

Additional substantially pure E-norelgestromin and substantially pure Z-norelgestromin may be obtained from the dichloromethane mother liquor by column chromatography.

The substantially pure E-norelgestromin and substantially pure Z-norelgestromin is optionally further purified by recrystallization to increase the purity, e.g., to obtain an isomeric purity of greater than 99%.

In another embodiment, the present invention is directed to a process of preparing d-(17α)-13-ethyl-17-hydroxy-18,19-dinorpregn-4-ene-20-yn-3-one-(3E)-oxime comprising stirring a mixture of E and Z isomers of norelgestromin of any ratio with either hydroxylammonium acetate or with a hydroxylammonium salt and up to one equivalent of the alkali metal acetate per hydroxylammonium salt, in acetic acid containing not more than 50 mass percent of water; at about 15° C. to about 30° C. for about 24 to about 72 hours. The E-norelgestromin may be isolated using standard techniques, for example, addition of additional water to isolate. Optionally, the process further comprises purifying the obtained E-norelgestromin by, for example, recrystallization, column chromatography, or flash chromatography.

The substantially pure E-isomer can be produced from any E/Z isomeric mixture. In another embodiment, the substantially pure Z-isomer of norelgestromin can be converted into the substantially pure E-isomer of norelgestromin according the described process.

For example, the reaction mixture is stirred for approximately 24 to 72 hours, preferably for 48 hours, after consumption of the starting material, without isolating the formed oxime, and carrying out the reaction under the above reaction conditions, using glacial acetic acid or 85% aqueous acetic acid as solvent, and the formed product is filtered off or isolated after addition of water. Then the obtained isomeric mixture contains the E/Z isomers of norelgestromin in a ratio of about 94:6.

In another embodiment, the present invention is directed to a process of preparing d-(17α)-13-ethyl-17-hydroxy-18,19-dinorpregn-4-ene-20-yn-3-one-(3Z)-oxime comprising stirring a mixture of E/Z isomers of norelgestromin of any ratio in dichloromethane; filtering from the dichloromethane solution the insoluble (3E)-oxime isomer of Formula I; and purifying the filtrate, for example by column chromatography, using silica gel as adsorbent and a mixture of apolar-polar solvents as eluent to give the (3Z)-oxime of Formula II. In a further embodiment, the chromatography is performed using silica gel as adsorbent and a mixture of apolar-polar solvents as eluent. The Z-norelgestromin can optionally be further purified by recrystallization from a suitable solvent.

Any solvent or mixture of solvents that allows the separation of the isomers by column chromatography can be used. Such solvents include but are not necessarily limited to hexanes, acetone, toluene, chloroform, methanol, ethanol, isopranol, ethyl acetate, and the like. Any solvent or mixture of solvents that allows recrystallization of the isomers can be used. Such solvents include but are not necessarily limited to isopranol, methanol, ethanol, acetonitrile, etc.

In one respect, this process can be used to prepare each of the oxime isomers of norelgestromin. The E-norelgestromin is isolated as a precipitate from the dichlormethane solution. The E-norelgestromin is then further purified, for example, by recrystallization using as suitable solvent.

In another embodiment, norelgestromin is prepared by hydrolyzing the acetate group at position 17 of the 3E- or 3Z-isomer of norgestimate in alcoholic solution, e.g., methanol, ethanol, isopropanol, and butanol, with equivalent of metal hydroxide to have the obtained product, of the same configuration as the starting material and isolating it to give the (3E)-oxime isomer of the Formula I or the (3Z)-oxime isomer of Formula II. In another embodiment, the hydrolysis is carried out at a temperature of about 5 to about 30° C. In one embodiment of this process, the hydrolysis is carried out on substantially pure 3E-norgestimate or substantially pure 3Z-norgestimate. In this way, the process yields substantially pure 3E-norelgestromnin or substantially pure 3Z-norelgestromin, respectively. In a further embodiment, the process further comprises purifying the norelgestromin by, for example, recrystallization. Suitable metal hydroxides include alkali metal hydroxide and alkaline earth metal hydroxides. Suitable alkali metal hydroxides for the hydrolysis of norgestimate include but are not limited to sodium hydroxide, and lithium hydroxide. Preferably, lithium hydroxide monohydrate is used. Various solvents can be used for the reaction. Such solvents include methanol, ethanol, isopropanol, tetrahydrofuran, and the like and mixtures thereof. In a preferred embodiment, the reaction is carried out in methanol.

According to this embodiment, the substantially pure E- or Z-oxime isomers can be obtained from the known d-(17α)-13-ethyl-17-(acetyloxy)-18,19-dinorpregn-4-ene-20-yn-3-one-(3E)- or -(3Z)-oxime by hydrolyzing the acetoxy group at position 17. The stereochemical purity does not substantially change under the mild reaction conditions of hydrolysis according to the present invention. In another aspect, the E/Z isomeric mixture of norgestimate can separated by a known chromatographical method (see for example J. Chromatogr., 635, 342-345 (1993)); the acetate group at position 17 of the substantially pure E- or Z-isomer oxime is then hydrolyzed according to the present invention by a metal hydroxide, such as but not limited to lithium hydroxide or sodium hydroxide in alcoholic solution under mild conditions, preferably at about 5 to about 20° C. If the hydrolysis is carried out under the conditions of the present invention, the stereochemistry of the hydroxyl group of the oxime group does not substantially change. D-(17α)-13-ethyl-17-(acetyloxy)-18,19-dinorpregn-4-ene-20-yn-3-one-(3E)- and -(3Z)-oximes are known in the art (see for example, J. Chromatography 635:342-345 (1993)).

In another embodiment, the present invention is directed to a process of preparing a mixture of oxime isomers of norelgestromin comprising reacting d-norgestrel with about 1.2 to about 5 mol equivalents of hydroxylammonium acetate; in acetic acid containing not more than 50 mass percent of water; at about 15° C. to about 50° C.; for about 15 minutes to about 45 minutes; and diluting with about a 10-fold volume of water to yield a precipitated isomeric mixture of E/Z norelgestromin isomers. In one embodiment, the E and Z isomers are produced in a ratio of about 56:44 to about 64:36.

In another embodiment, the present invention is directed to a process of preparing a mixture of oxime isomers of norelgestromin comprising reacting d-norgestrel with 1.2 to about 5 mol equivalents of a hydroxylammonium salt along with not more than 1 mol equivalent (based on the hydroxylammonium salt) of an alkali metal acetate; in acetic acid containing not more than 50 mass percent of water; at about 15° C. to about 50° C.; for about 15 minutes to about 45 minutes; and diluting with about a 10-fold volume of water to yield a precipitated isomeric mixture of E/Z norelgestromin isomers. In one embodiment, the E and Z isomers are produced in a ratio of about 56:44 to about 64:36.

Suitable hydroxylammonium salts include hydroxylammonium chloride and hydroxylamine nitrate, hydroxylamine phosphate, and hydroxylamine sulfate. Of course, other hydroxylammonium salts may be used in the present invention.

According to certain embodiments of the present invention, if the formation of oximes is carried out with hydroxylammonium hydrochloride and sodium acetate, or with hydroxylammonium acetate in glacial acetic acid or in aqueous acetic acid, then the ratio of E/Z isomers in the obtained crude isomeric mixture can be varied between 56:44 and 94:6 depending on the further treatment of the mixture. This allows for example the isolation of E-oxime isomer directly from the reaction mixture, but also helps in isolating the Z-oxime isomer by column chromatography, for example from the 56:44 mixture because this ratio can be changed to a different ratio, for example about 65.5 to about 34.5, after stirring in dichloromethane. The Z isomer can easily be isolated from this mixture, for example by column chromatography.

One embodiment of the process according to our invention can preferably be carried out as follows. From about 1.2 to about 5 mol equivalent (calculated for 1 mol of d-norgestrel) of hydroxylammonium chloride and not more than one equivalent of the latter of sodium acetate are suspended in glacial acetic acid, and the obtained suspension (sodium chloride precipitates) is stirred for 30 min. Then the sodium chloride is filtered off. d-Norgestrel is added to the filtrate, and the reaction mixture is stirred until the reaction is complete (monitored by TLC). The reaction mixture is then diluted with water. The precipitated norelgestromin is filtered off, washed with water, dried, and recrystallized.

According to another embodiment of our invention, the sodium chloride is not filtered off because, after addition of water, it dissolves and does not influence the yield and the quality of the product.

In certain embodiments, the E/Z ratio of the obtained mixture of norelgestromin oximes is about 60:40.

In other embodiments, hydroxylammonium acetate prepared in advance can also be used as a suitable oximation reagent.

According to another embodiment of the invention, for example, a 60:40 mixture of E/Z isomers or alternatively pure Z-isomer is suspended in acetic acid containing hydroxylammonium hydrochloride and not more than one equivalent of the latter of sodium acetate and the above reaction conditions are applied. In this case, an isomeric mixture is obtained containing the E/Z isomers in a ratio of about 90:10 to about 96:4.

In another embodiment, the oximation reaction is carried out by keeping the reaction mixture homogeneous, and immediately after consumption of the starting material, the reaction mixture is diluted with water. The precipitated solid product is isolated, and then the isomeric ratio of the obtained mixture is 56:44 E/Z oximes. This isomeric mixture can then be stirred with dichloromethane as described above. In this instance, the less soluble E-isomer can be filtered off, and the isomeric ratio in the filtrate can be enriched for the Z-isomer (about E/Z=33:77), which assists in the isolation of Z-isomer by column chromatography.

In certain embodiments, the separation of E- and Z-isomers of norelgestromin is carried out by column chromatography using silica gel as adsorbent and starting the elution with a predominantly apolar mixture of solvents and gradually increasing the concentration of the more polar solvent. The fractions containing the same isomer are concentrated and the residue is recrystallized.

According to the process of our invention, the pure E-oxime isomer can be produced on industrial scale. The separation of Z-oxime isomer can be economical because the ratio of E/Z isomers can be varied for the Z-isomer oxime and from this mixture the Z-isomer can be isolated by column chromatography. In another embodiment, the pure Z-oxime isomer can be produced on industrial scale.

In certain instances, the product of each step of the process is isolated and purified, for example by recrystallization. In other instances, the only final product of the E or Z norelgestromin is recrystallized.

In another embodiment, the process according to our invention is the following:

a) reacting d-norgestrel with 1.2-5 mol of hydroxylammonium acetate, or with a hydroxylammonium salt in the presence of not more than one mole equivalent of alkali metal acetate calculated on 1 mol of d-norgestrel, in acetic acid containing not more than 50 mass percent of water, at 15-50° C. for 15-45, min and after that the obtained reaction mixture containing the isomeric mixture of norelgestromin
  1) is diluted with about a 10-fold volume of water and the precipitated isomeric mixture is isolated to give an E/Z mixture of isomers in a ratio of about 56:44-64:36, or
  2) after addition of about 10-25 volume percent of water it is stirred at 10-30° C. for 24-72 h, water is added to the reaction mixture and the precipitated product is isolated to give the (3E)-oxime isomer of Formula I, or
  3) after addition of about 10-fold volume of water the precipitated isomeric mixture is isolated and stirred in dichloromethane, the insoluble (3E)-oxime isomer of Formula I is filtered off, the filtrate is purified by column chromatography using silica gel as adsorbent and a mixture of apolar-polar solvents as eluent to give the (3Z)-oxime of Formula II, or b) stirring a mixture of E/Z isomers of norelgestromin of any ratio
  1) with hydroxylammonium acetate, or with a hydroxylammonium salt and not more than one equivalent of alkali metal acetate, in acetic acid containing not more than 50 mass percent of water, at 15-30° C. for 24-72 hours and, in certain embodiments after addition of additional water, isolating the product to give the (3E)-oxime isomer of the Formula I, or
  2) in dichloromethane, filtering off the insoluble (3E)-oxime isomer of Formula I, purifying the filtrate by column chromatography using silica gel as adsorbent and a mixture of apolar-polar solvents as eluent to give the (3Z)-oxime of Formula II, or c) hydrolyzing the acetate group at position 17 of the 3E- or 3Z-isomer of norgestimate in alcoholic solution with an equivalent of alkali metal hydroxide at 5-30° C. to provide the obtained product, of the same configuration as the starting material and isolating it to give the (3E)-oxime isomer of the Formula I or the (3Z)-oxime isomer of Formula II;

and optionally purifying the isomers of Formula I and II obtained according to processes a)-c) by crystallization.

In certain embodiments, the E or Z oxime isomer of norelgestromin is prepared having isomeric purity of at least 70%. In other embodiments, the E or Z oxime isomer of norelgestromin is prepared having isomeric purity of at least 80%. Other suitable levels of purity that can be obtained according to the present invention include but are not limited to at least about 75%, 85%, 90%, 95%, 96%, 97%, 98%, and 99%.

Another aspect of the present invention relates to a process for preparing E or Z oxime isomers of norelgestromin on a large scale. An advantage of the process described herein is that multigram quantities the individual oxime isomers can be prepared in a safe and economical fashion. The process of the invention can be readily adapted for industrial synthesis of norelgestromin oxime isomers for use in mass-produced pharmaceutical compositions. For example, in one embodiment, the yield of the process is at least about 10 grams, about 20 grams, about 30 grams, or about 40 grams. In a preferred embodiment, the process further comprises recrystallizing the norelgestromin. The yield refers to the amount of product obtained from a single batch. In other embodiments, the yield of the process is from about 2 grams to about 50 grams.

In another embodiment, the processes described herein can be used in conjunction with, as a part of, or in addition to, in whole or in part, the process described in copending application Ser. No. 10/879,708 titled "Process for the synthesis of high purity d-(17α)-13-ethyl-17-hydroxy-18,19-dinorpregn-4-ene-20-yn-3-one-oxime," filed Jun. 30, 2004, which is incorporated herein by reference in its entirety. For example, a process described therein for preparing a high purity norelgestromin can be used in conjunction with the method described herein for preparing a substantially pure E- or Z-oxime isomer of norelgestromin.

Pure Isomers

In a further embodiment, the present invention is directed to the isolated, substantially pure compounds of Formula I and II. Prior to the present invention, the characteristic physical properties of these compounds in pure form had not been characterized. Nor had their structures been unambiguously proven.

Furthermore, the present invention is directed to substantially pure, pharmaceutically acceptable amounts of E- and Z-isomers of norelgestromin. For example, in one embodiment, the present invention is directed to substantially pure, pharmaceutically acceptable E- and Z-isomers of norelgestromin in an amount of at least 1 gram. Other suitable amounts include 5, 10, 15, 20, 30, 40, and 50 grams.

Compositions

An additional aspect of the present invention is directed to a composition comprising a substantially pure oxime isomer of norelgestromin. A composition according to the present invention includes a pharmaceutical composition comprising a substantially pure oxime isomer of norelgestromin and one or more pharmaceutically acceptable excipients. Pharmaceutical compositions of the present invention may be formulated, as is well known in the prior art, such as by reference to known compilations as Remington's Pharmaceutical Sciences, Mack Publishing Co., Easton, Pa., USA.

In one embodiment, the invention is directed to a pharmaceutical composition comprising substantially pure Z-norelgestromin and a pharmaceutically acceptable carrier and/or excipient. In another embodiment, the pharmaceutical composition comprises substantially pure E-norelgestromin and a pharmaceutically acceptable carrier and/or excipient. The amount of norelgestromin present in the composition can vary but is generally an amount effective to treat a condition as described herein or known in the art. Other dosage amounts are described herein.

The pharmaceutical compositions of the invention can be administered to any animal that can experience the beneficial effects of the compounds of the invention. Foremost among such animals are humans, although the invention is not intended to be so limited. Preferably, the composition of the present invention is administered to a woman. Other animals include bovines, canines, equines, and felines.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. The dosage administered may be dependent upon the age, health, and weight of the recipient, the kind of concurrent treatment, if any, the frequency of treatment, and the nature of the effect desired.

The pharmaceutical compositions of the present invention can preferably be tablets, dragées, or transdermal patches. The tablets can contain, in addition to the active ingredients, the usual carriers, excipients, diluents, stabilizers, flavoring or aromatizers, as well as formulation promoting or, formulation-providing additives. The formulation of tablets can be carried out by methods conventionally used in practice. The preparation of dragées can be carried out, for example, by coating the dragées cores, prepared similarly to tablets, according to the usual methods.

In one embodiment, the pharmaceutical composition of the present invention is a tablet comprising an amount of substantially pure E- or Z-norelgestromin effective to provide birth control or contraception.

In another embodiment, the dosage form is a tablet comprising substantially pure Z-norelgestromin, for example about 0.1 to about 0.5 mg, preferably about 0.25 mg, and ethinyl estradiol, for example about 10 to about 50 µg, preferably about 35 µg. The tablet further comprises suitable excipients, such as lactose, microcrystalline cellulose, colloid silicon dioxide AEROSIL® (Evonik Degussa GmbH Ltd., Hanau, Del.), and magnesium stearate.

In another embodiment, the tablet is formed by spray-drying a solution of substantially pure Z-norelgestromin and ethinyl estradiol in solvent, such as ethanol, on a homogeneous mixture of lactose and cornstarch. The solvent is removed from the mixture by fluidization drying. The obtained powder mixture containing the active ingredients is granulated according to known methods and formed into tablets. Other suitable excipients include polyvinylpyrrolidone (PVP), colloid silicon dioxide, and magnesium stearate.

In another embodiment, the tablet comprises the substantially pure Z-isomer of norelgestromin, for example about 250 µg; ethinyl estradiol, for example about 35 µg; polyvinylpyrrolidone, for example about 2 mg; lactose, for example about 75 mg; cornstarch, for example about 20.5 mg; colloid silicon dioxide, for example about 1 mg; and magnesium stearate, for example about 0.5 mg.

In another embodiment, the pharmaceutical composition is a transdermal patch comprising a substantially pure oxime isomer of norelgestromin. The patches can preferably be matrix-type transdermal patches consisting of 3 layers. Their external layer is a membrane, which is impermeable for the active ingredients and other components of the matrix, consisting of PVC, polyethylene, polypropylene or polyurethane film. The matrix containing the active ingredients is disposed on this external layer. The matrix contains pressure sensitive adhesive component, which can be polyacrylate, polydimethylsiloxane or polyisobutylene. One of these adhesives is mixed with the active ingredients and the polyvinylpyrrolidone auxiliary material, which inhibits crystallization. Auxiliaries (enhancers), which promote the absorption of steroids through the skin, are preferably dispersed in the matrix as well. These components can be for example esters of aliphatic alcohols, such as lauryl lactate, oleic acid, etc. The so obtained dispersion is disposed on the external layer of the patch and dried.

The matrix of the patch is covered by the third layer of the plaster, the protective layer, which can be for example a polyethylene terephthalate film. The protective layer should be removed before the application of the patch to the skin.

In other embodiments, the transdermal matrix comprises one or more permeation enhancers to increase the permeability of the norlegestromin and the optional estrogen through the skin. Examples of skin permeation enhancers that may be included in the matrix are described in U.S. Pat. Nos. 5,059,426, 4,973,468, 4,906,463 and 4,906,169, and include, but are not limited to, lactate esters of $C_{12}$ to $C_{18}$ aliphatic alcohols, lauryl lactate, oleic acid, or polyethylene glycol monolaurate. The amount of permeation enhancer included in the matrix depends upon the particular enhancer(s) used. In most instances, then enhancer constitutes about 1 to about 20% by weight of the matrix.

Broadly, patches are devices that contain, at a minimum, a drug reservoir matrix for holding the drug and metering the drug deposition or delivery to the skin, a backing, and an adhesive layer for adhering the device to the patient. The device may contain other layers such as a drug release rate controlling layer for modulating delivery rate, and the like. The device may contain permeation enhancers to increase the rate of penetration of drugs across the skin. Patches are well known and understood by persons skilled in the art. Patches are now employed in marketed products for the administration of certain progestogen. Specific patches and even their application to steroids of the type described herein are described in U.S. Pat. Nos. 5,474,783; 5,656,286; 5,958,446; 6,024,976; 5,252,334; 5,006,342; and 4,906,463, each of which is fully incorporated by reference herein. Other suitable transdermal dosage forms are disclosed in Published U.S. Patent Appln. Pub. No. 20040043171, which is incorporated by reference in its entirety herein.

In certain embodiments, the patch of the invention has a basal surface area (i.e., the area in diffusional contact with the skin) between 10 and 50 $cm^2$. Of course, various sizes and shapes of patches are understood to be within the scope of the present invention.

In one embodiment, the invention comprises a matrix type transdermal patch of 3 layers containing 6.0 mg of substantially pure E-isomer of norelgestromin and 0.75 mg of ethinyl estradiol. For every patch unit, the composition comprises 6.0 mg substantially pure of E-isomer of norelgestromin, 0.75 mg of ethinyl estradiol, 25 mg of polyvinylpyrrolidone, 20 mg of lauryl lactate, and 248 mg of polyisobutylene.

In another embodiment, the matrix type transdermal patch of 3 layers contains about 6.0 mg of substantially pure E-isomer of norelgestromin and about 0.75 mg of ethinyl estradiol. In another embodiment, the composition comprises 261 mg of polydimethylsiloxane and 17 mg of polyvinylpyrrolidone, 15 mg of methyl laureate, 6.0 mg of substantially pure E-isomer of norelgestromin, and 0.75 mg of ethinyl estradiol.

In one embodiment, the dosage form, preferably the transdermal form, comprises an amount of active ingredients such that about 150 μg to about 350 μg, preferably 175 μg to about 350 μg, of substantially pure E-norelegestromin, and about 5 μg to about 45 μg, preferably about 10 to about 35 μg, more preferably about 20 μg of ethinyl estradiol are delivered per day.

In one embodiment, the dosage form, preferably the transdermal form, comprises an amount of active ingredients such that about 150 μg to about 350 μg, preferably 175 μg to about 350 μg, of substantially pure Z-norelegestromin, and about 5 μg to about 45 μg, preferably about 10 to about 35 μg, more preferably about 20 μg of ethinyl estradiol are delivered per day.

In another embodiment, the invention is directed to a transdermal patch for providing hormone replacement therapy in a woman comprising: a) a backing layer; and b) a non-acrylate containing matrix layer underlying the backing layer, the matrix layer comprising a mixture of substantially pure E-norelgestromin, an estrogen selected from the group consisting of ethinyl estradiol and 17-β-estradiol, lauryl lactate, and a pressure sensitive adhesive consisting essentially of polyisobutylene and an aliphatic tackifier, and being adapted to be in diffusional communication with the skin of a woman and to co-administer a therapeutic amount of said substantially pure E-norelgestromin and said estrogen to said skin.

In another embodiment, the invention is directed to a transdermal patch for providing hormone replacement therapy in a woman comprising: a) a backing layer; and b) a non-acrylate containing matrix layer underlying the backing layer, the matrix layer comprising a mixture of substantially pure Z-norelgestromin, an estrogen selected from the group consisting of ethinyl estradiol and 17-β-estradiol, lauryl lactate, and a pressure sensitive adhesive consisting essentially of polyisobutylene and an aliphatic tackifier, and being adapted to be in diffusional communication with the skin of a woman and to co-administer a therapeutic amount of said substantially pure Z-norelgestromin and said estrogen to said skin.

Other suitable transdermal dosage forms include those described in U.S. Pat. Nos. 5,876,746; 5,972,377; and 6,071,531, each of which is fully incorporated by reference herein. The dosage forms disclosed in these patents can be used in accordance with the present invention by replacing the 17-deacetylnorgestimate with the substantially pure E- or Z-norelgestromin of the present invention.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is within the skill of the artisan, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Pharmaceutical excipients are well known in the art. Suitable excipients include fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, for example, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

In another embodiment, the pharmaceutical composition of the present invention is a vaginal ring. Vaginal rings are generally devices having an elastomeric portion or body into which the active steroid is dispersed and which acts as a reservoir and meter for the diffusion of active to the lining of the vagina. The ring may be composed entirely of elastomer with steroid homogenously dispersed throughout as described in U.S. Pat. No. 3,545,397. The ring may have an inert inner core surrounded by an active containing elastomeric layer as described in U.S. Pat. No. 4,012,496. The ring may have an elastomeric active containing inner core surrounded by a thin elastomeric layer initially containing no active. The ring may have an inert core, surrounded by an active containing elastomeric layer and further surrounded by an elastomeric outer layer of variable thickness initially containing no active as described in U.S. Pat. No. 4,292,965. The elastomer, the layered design of the ring, its surface area, the concentration of active, the nature of the active, etc., all combine to determine the release rate of active. Rings are well known and understood by persons skilled in the art. Rings are now employed in marketed products for the administration of certain steroids. Other suitable rings include those described in U.S. Pat. Nos. 4,871,543 and 5,188,835, each of which is fully incorporated by reference herein.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions, and cyclodextrin inclusion complexes.

In other embodiments, the compounds of the invention are administered parenterally as an injectable dosage form in a physiologically acceptable diluent such as sterile liquids or mixtures thereof, including water, saline, aqueous dextrose and other pharmaceutically acceptable sugar solutions, alcohols such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol)400, a pharmaceutically acceptable oil, fatty acid, fatty acid ester or glyceride, or an acetylated fatty acid glyceride with or without the addition of a pharmaceutically acceptable surfactant, such as a soap or detergent, suspending agent such as pectin, carbomers, methylcellulose, hydroxypropylmethylcellulose, or carboxymethylcellulose, an emulsifying agent or pharmaceutical adjuvants. In all cases, the form must be sterile and must be fluid to provide easy syringability.

Pharmaceutically acceptable oils which are useful in the formulation herein include those of petroleum, animal, vegetable or synthetic origin, including peanut oil, soybean oil, sesame oil, cottonseed oil, olive oil, sunflower oil, petrolatum, and mineral oil. Fatty acids which may be used include oleic acid, stearic acid, and isostearic acid, while the fatty acid esters useful herein may include ethyl oleate and isopropyl myristate. Suitable soaps include fatty acid alkali metal, ammonium, and triethanolamine salts.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400. Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized.

Compositions for vaginal administration are in one embodiment suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

In other embodiments, the compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used.

Method of Treatment

In a further aspect of the invention, the compounds and compositions described herein are used to treat one or more ailments, conditions, diseases, or physiological states. The present invention comprises administering to a subject in need an effective amount of substantially pure E- or Z-norelgestromin.

In one embodiment, the norelgestromin is adminstered via a transdermal patch. The transdermal patch of the invention can provide contraception for females, preferably women. The patch is also suitable for hormone replacement therapy.

In certain embodiments, the patch delivers substantially pure E- or Z-norelgestromin and, optionally an estrogen, to the skin continuously for an extended time period, for example 1-7 days and preferably for 7 days.

In one embodiment, the effective dose of substantially pure E- or Z-norelgestromin for inhibiting ovulation is normally in the range of about 150 to about 350 µg/day, preferably from about 175 to about 300 µg/day, and more preferably from about 175 to about 250 µg/day. The effective dose of estrogen for inhibiting ovulation depends on the particular estrogen being co-administered. For instance, when the estrogen is ethinyl estradiol, the dose is normally at least 10 µg/day, preferably from about 10 to 35 µg/day, and most preferably approximately 20 µg/day. In other embodiments, the typical doses are from about 20 µg/day to about 200 µg/day, and preferably from about 30 µg/day to 150 µg/day of ethinyl estradiol.

When the patches are worn for contraception, a patch is typically placed on the skin on the fifth day of the menstrual cycle, and replaced as needed until 21 days of wearing have elapsed. For instance, in the case of a 7-day patch, three patches are generally required to deliver the drug(s) for the 21-day period. If desired, a placebo patch may be worn thereafter until the fifth day of the succeeding menstrual cycle. This regimen is repeated for each menstrual cycle.

In certain embodiments, an effective amount administered is from about 150 to about 350 µg/day and preferably from about 175 to about 300 µg/day of substantially pure E- or Z-norelgestromin. In one aspect, the substantially pure E- or Z-norelgestromin is co-administered with an ovulation inhibiting amount of an estrogen, such as ethinyl estradiol. In other embodiments, an effective amount is from about 150 to about 350 µg/day and preferably from about 175 to 300 µg/day of substantially pure E- or Z-norelgestromin and from 10 to 35 µg/day of ethinyl estradiol.

In one embodiment, the composition of the present invention is intravaginally administered, by use of a ring. Broadly, rings are devices having an elastomeric portion or body into which the active steroid is dispersed and which acts as a reservoir and meter for the diffusion of active to the lining of the vagina.

In one embodiment, the contraceptive regimen according to the present invention is a progestin-only contraceptive regimen in which the substantially pure E- or Z-oxime isomer of norelgestromin is continuously administered in a sufficient dose to have a contraceptive effect, and the regimen is administered cycle after cycle to a menstruating female to achieve a long term contraceptive effect. In such regimens, no estrogen is administered, and there is no period of time without hormone administration to allow for menstruation. Menstruating female is intended to refer to fertile women of child-bearing age. The method of administration might be transdermal, vaginal, or oral. Where administration is transdermal, a suitable patch is continuously worn with replacement as required. Where administration is vaginal, a suitable vaginal device, such as a ring, is continuously inserted with replacement as required. Where administration is oral, daily oral dosage units are administered.

In certain embodiments, the cycle of administration usually lasts 28 days or more, but it may be longer, for example up to 60 and even 90 days, or shorter down to 21 days. The cycle optionally includes a regimen in which there is a day to day or week to week variation in the dose of norelegestromin administered according to a set pattern. In such a case, the regimen, including variation of dose, is repeated in cycle following cycle. Alternatively, the cycle may also be a regimen in which there is no variation in the dose of the active administered. In such a case, the cycle is a convention representing a convenient unit of administration or sale. In either case, a contraceptive product utilizing the contraceptive regimen in question is prescribed, sold, and administered in units of cycles. The contraceptive product based on a cycle might be 1 to 10 vaginal rings that are inserted and then replaced every 7, 14, or 21 days according to their design. The contraceptive product based on a cycle might be 2 to 10 transdermal patches that are attached and then replaced every 7, 10, or 14 days according to their design. The contraceptive product based on a cycle might be 21, 28, 56, or more tablets that are orally administered daily.

In the case of a daily oral tablet, there is administered in certain embodiments a preferred dose of substantially pure E- or Z-norelgestromin between about 30 µg to about 500 µg and more preferably between about 150 µg to about 300 µg. Specific daily oral tablets contain, for example, 100, 125, 180, 215, or 250 µg of substantially pure E- or Z-norelgestromin. In the case of a vaginal ring, a certain embodiment of a ring delivers to systemic circulation a daily dose of substantially pure E- or Z-norelgestromin between about 20 µg to about 300 µg and more preferably between about 90 µg to about 200 µg. A specific vaginal ring might be inserted for one week and deliver to systemic circulation in that period of time an average daily dose of 60, 75, 100, 125 or 150 µg of substantially pure E- or Z-norelgestromin. In the case of a transdermal patch, a preferred patch delivers to systemic circulation a daily dose of substantially pure E- or Z-norelgestromin between about 20 µg to about 300 µg and more preferably between about 90 µg to about 200 µg. A specific patch might be worn for one week and deliver to systemic circulation in that period of time an average daily dose of 60, 75, 100, 125, or 150 µg of substantially pure E- or Z-norelgestromin.

Other suitable regimens are disclosed in U.S. Published Patent Applications Pub. Nos. 20030229057; 20030225048; 20030225047; and 20030219471, each of which is fully incorporated by reference herein, and can be adapted to deliver the substantially pure E- or Z-norelgestromin In one embodiment, the substantially pure E- or Z-norelgestromin is administered in an amount effective to produce a contraceptive effect. According to another embodiment of the present invention, the substantially pure E- or Z-norelgestromin is administered in an amount which is an effective breast protective amount. For example, sufficient substantially pure E- or Z-norelgestromin may be administered such that it is at least equivalent in both contraceptive and breast protecting effect to about 0.030 mg to about 0.750 mg of orally administered norgestimate. In another example, there is administered sufficient active compound to provide for, during a substantial portion of each day, a substantial suppression of sulfatase activity, for example, of 50% or greater and preferably of 67% or greater and most preferably of 75% or greater. A substantial portion of a day is intended to mean a period of at least 4 hours, but within the invention might mean a period of at least 8 hours or 12 hours or even 24 hours.

In another embodiment, the invention provides a method of treating a female in need of hormone replacement therapy comprising transdermally administering to said female a pharmaceutical patch regimen series consisting essentially of a series of transdermal patches arranged in alternating phases of dominant hormone activity of from about one day to about four days, said phases being selected from estrogen dominant activity phases and progestin dominant activity phases. Each of these phases can comprise at least one patch which is applied and removed in accordance with the particular dominant phase activity, wherein the estrogen dominant activity phase contains an amount of a substance exhibiting estrogen activity sufficient to promote the development of progestin receptors in the endometrium of said female, or an amount of a substance exhibiting estrogen activity sufficient to promote the development of progestin receptors in the endometrium of said female and an amount of a substance exhibiting progestin activity; and wherein the progestin dominant activity phases contain an amount of a substance exhibiting estrogen activity and an amount of substantially pure E- or Z-norelgestromin sufficient to antagonize the effect of estrogen on the endometrium of said female. The estrogen and progestin are selected from transdermally administrable hormones. Such a general method is described in further detail in U.S. Pat. No. 5,422,119, which is hereby fully incorporated by reference herein.

The present invention also provides a method of hormone replacement therapy. The substantially pure E- or Z-norelgestromin can be used in a suitable hormone replacement therapy regimen, either alone or in combination with other hormones. For example, in one embodiment, the method provides from about 150 to about 350 μg/day, and preferably from about 175 to about 300 μg/day substantially pure E- or Z-norelgestromin co-administered with from about 5 to about 45 μg/day and preferably from about 10 to about 35 μg/day of an ethinyl estradiol. In an alternative embodiment, the method provides from about 200 to about 350 μg/day, and preferably from about 175 to about 300 μg/day substantially pure E- or Z-norelgestromin co-administered with from about 20 to about 175 μg/day and preferably from about 30 to about 150 μg/day of 17-p-estradiol. In other embodiments, the method of providing hormone replacement therapy is carried out by administering the compositions via a transdermal patch applied to the skin for seven days.

DEFINITIONS

As used herein, the term "isomer of norelgestromin" refers to one of the oxime isomers of norelgestromin, i.e., d-(17α)-13-ethyl-17-hydroxy-18,19-dinorpregn-4-ene-20-yn-3-one-(3E)-oxime or d-(17α)-13-ethyl-17-hydroxy-18,19-dinorpregn-4-ene-20-yn-3-one-(3Z)-oxime, as shown in Formulas I and II respectively.

As used herein, the term "E-norelgestromin" refers to d-(17α)-13-ethyl-17-hydroxy-18,19-dinorpregn-4-ene-20-yn-3-one-(3E)-oxime as shown in Formula I. Other names synonymous with this term include "the E-isomer of norelgestromin," "the E-oxime isomer of norelgestromin," and variants thereof.

As used herein, the term "Z-norelgestromin" refers to d-(17α)-13-ethyl-17-hydroxy-18,19-dinorpregn-4-ene-20-yn-3-one-(3Z)-oxime as shown in Formula II. Other names synonymous with this term include "the Z-isomer of norelgestromin," "the Z-oxime isomer of norelgestromin," and variants thereof.

The term "substantially pure," as used herein, refers to a compound being at least about 90% isomerically pure with respect to the oxime isomers. For example, substantially pure Z-norelgestromin contains no more than about 10% E-norelgestromin isomer. Likewise, for example, substantially pure E-norelgestromin contains no more than about 10% Z-norelgestromin isomer. In other embodiments, the E-norelgestromin or Z-norelgestromin isomer contains no more than 5%, 2%, or 1% of the Z-norelgestromin or E-norelgestromin isomer, respectively.

The invention is illustrated by the following examples, which are not meant to limit the scope of the invention.

Example 1 d-(17α)-13-Ethyl-17-hydroxy-18,19-dinorpregn-4-ene-20-yn-3-one-(E/Z)-oxime 34.7 g (0.5 mol) of hydroxylammonium hydrochloride and 34 g (0.41 mol) of sodium acetate are suspended in 500 mL of glacial acetic acid, and after stirring for 1 hour 31.2 g (0.1 mol) of d-norgestrel is added under nitrogen. The heterogeneous reaction mixture is stirred until the reaction is complete and then poured into 3000 mL of water. The precipitated product is filtered off, washed successively with water, 5% aqueous ammonium hydroxide solution, water until neutral then dried below 60° C. under vacuum.

The obtained crude product is dissolved in 320 mL of ethanol, and decolorized with charcoal. After filtering the charcoal, the solution is concentrated to a volume of 10% of the original. The residue is cooled to 0° C. and filtered after 5 h. The solid material is washed with ethanol and dried to yield 29.4 g (90%) of the title compound. Mp.: 110-130° C. (a mixture of oxime isomers). The ratio of the oxime isomers: E-oxime=58%; Z-oxime=42%.

Example 2 d-(17α)-13-Ethyl-17-hydroxy-18,19-dinorpregn-4-ene-20-yn-3-one-(3E)-oxime

Under nitrogen, to a vigorously stirred suspension of 2.5 g (0.035 mol) of hydroxylammonium hydrochloride, 2 g (0.024 mol) of sodium acetate and 55 mL of 70% aqueous acetic acid, 5 g (0.016 mol) of d-norgestrel is added and stirring is continued for 50 h. The reaction mixture is poured into 500 mL of water. The precipitated product is filtered off, washed successively with water, 5% aqueous ammonium hydroxide solution, and water until neutral, and then dried below 60° C. The obtained crude product (the ratio of the oxime isomers: E-oxime=94.5%; Z-oxime=5.5%) is recrystallized from dichloromethane to yield 4.65 g (88.7%) of the title compound, the pure E-isomer. Mp.: 198-200° C.

Example 3 d-(17α)-13-Ethyl-17-hydroxy-18,19-dinorpregn-4-ene-20-yn-3-one-(3E)-oxime 5 g (0.07 mol) of hydroxylammonium hydrochloride and 5.8 g (0.07 mol) of sodium acetate are suspended in 100 mL of glacial acetic acid. The suspension is stirred for 1 h, and the formed sodium chloride is filtered off. Under nitrogen, 10 g (0.032 mol) of d-norgestrel is added to the stirred filtrate and stirring is continued until the reaction is complete. Then 30 mL of water is added to the reaction mixture, and stirring is continued for a further 50 h. The reaction mixture is poured into 1000 mL of water. The precipitated product is filtered off, washed according to the method described in Example 2, and dried. The crude product is recrystallized from acetonitrile to yield 9.1 g (86.8%) of the title compound, the pure E-isomer. Mp.: 198-200° C.

Example 4 d-(17α)-13-Ethyl-17-hydroxy-18,19-dinorpregn-4-ene-20-yn-3-one-(3E)-oxime

Under nitrogen, to a vigorously stirred suspension of 10 g (0.027 mol) of d-(17α)-13-ethyl-17-hydroxy-18,19-dinorpregn-4-ene-20-yn-3-one-3(E/Z)-oxime (ratio of isomers: E-oxime 58%, Z-oxime 42%) and 100 mL of glacial acetic acid 2.5 g (0.035 mol) of hydroxylammonium hydrochloride and 2.9 g (0.035 mol) of sodium acetate in 20 mL of water are added. The reaction mixture is stirred for another 50 h and then poured into 1000 mL of water. The reaction mixture was treated as described in Example 2 to yield 9.6 g (96%) of the crude product. The obtained product (ratio of isomers: E-oxime 94%. Z-oxime 6%) is recrystallized from ethyl acetate according to the method described in Example 2 to yield 9.1 g (91%) of the title compound, the pure E-isomer. Mp.: 197-199° C.

Example 5 d-(17α)-13-Ethyl-17-hydroxy-18,19-dinorpregn-4-ene-20-yn-3-one-(3Z)-oxime

A suspension of 43.8 g (0.53 mol) of sodium acetate, 50 g (0.72 mol) of hydroxylammonium hydrochloride, and 100 mL of 90% aqueous acetic acid is vigorously stirred at room temperature for 1 h. The precipitated sodium chloride is filtered off, 100 g (0.32 mol) of d-norgestrel is added to the filtrate under nitrogen, and the resulting mixture is stirred for 1.5 h. During this time, the temperature of the reaction is allowed to rise to 45° C. The reaction mixture becomes homogeneous, which indicates that the reaction is complete. The reaction mixture is poured into 4000 mL of water. The precipitated product is filtered off, washed successively with water, 5% aqueous ammonium hydroxide solution, and then water until neutral, and then dried. The obtained 104 g isomeric mixture of oximes (ratio of isomers: E-oxime 57.4%, Z-oxime 42.6%) is vigorously stirred with 20-fold volume of dichloromethane for 30 min. The insoluble material is filtered off and dried below 60° C. to yield 45.6 g of product (ratio of isomers: E-oxime 94.4%, Z-oxime 4.6%.

The mother liquor obtained after isolating the above product is concentrated to yield 58 g of a mixture of isomers (Z-oxime 65.5%, E-oxime 33.2%). The residue obtained is dissolved in 2300 mL (40-fold) of dichloromethane and kept at 0-5° C. for 5 h. The precipitated crystalline product is filtered off, washed with dichloromethane, and dried to yield 17.6 g of product (ratio of isomers: E-oxime 9%, Z-oxime 91%).

The mother liquor obtained from the crystallization is also concentrated, and the residue (39 g) is purified by column chromatography using 700 g of silica gel as adsorbent and toluene followed by a more polar mixture of toluene-acetone as eluent. The fractions containing the same isomer are concentrated to yield 3.7 g of E-oxime (isomer purity: 94%) and 25.2 g of Z-oxime (isomer purity: 95%).

The corresponding crystals obtained by crystallization and by column chromatography are combined and recrystallized first from 20-fold volume of acetonitrile, and then from 23-fold volume of ethyl acetate to yield 29 g of Z-oxime (purity: 99.3%) and 38.4 g of E-oxime (purity: 99.7%). Mp: Z-oxime: 206-207° C., mp.: E-oxime: 199-200° C.

Specific rotations: Z-oxime: $[\alpha]^{20}_D$=+106.4° (c=0.5, CHCl$_3$); E-oxime: $[\alpha]^{20}_D$=1.6° (c=0.5, CHCl$_3$).

NMR data: Z-oxime: $^1$H NMR (500 MHz, DMSO-d$_6$ (TMS), δ (ppm)): 0.92 (3H, t, —CH$_2$—CH$_3$), 1.40 (2H, m, —CH$_2$—CH$_3$), 2.05 & 2.24 (2H, m & m H-2), 3.28 (1H, s, ≡CH), 5.23 (1H, s, 17-OH), 6.40 (1H, m, H-4), 10.12 (1H, s, =N—OH).

$^{13}$C NMR (125 MHz, DMSO-$_6$ (TMS), δ (ppm)): 9.4 (—CH$_2$—CH$_3$), 18.3 (—CH$_2$—CH$_3$), 26.9 (C-2), 79.6 (C-17), 89.1, (—C≡), 74.9 (≡CH), 111.6 (C-4), 151.2 (C-3), 152.0 (C-5).

E-oxime: $^1$H NMR (500 MHz, DMSO-d$_6$ (TMS), δ (ppm)): 0.92 (3H, t, —CH$_2$—CH$_3$), 1.40 (2H, m, —CH$_2$—CH$_3$), 187 & 2.87 (2H, m & m, H-2), 3.28 (1H, s, ≡CH), 5.23 (1H, s, 17-OH), 5.78 (1H, m, H-4), 10.38 (1H, s, =N—OH).

$^{13}$C NMR (125 MHz, DMSO-d$_6$ (TMS), δ (ppm)): 9.4 (—CH$_2$—CH$_3$) 18.3 (—CH$_2$—CH$_3$) 20.6 (C-2) 79.6 (C-17), 89.1 (—C≡), 74.9 (≡CH), 118.6 (C-4), 154.3 (C-3), 148.1 (C-5).

Example 6 d-(17α)-13-Ethyl-17-hydroxy-18,19-dinorpregn-4-ene-20-yn-3-one-(3E)-oxime

Under nitrogen, to a vigorously stirred solution of 10 g (0.027 mol) of d-(17α)-13-ethyl-17-hydroxy-18,19-dinorpregn-4-ene-20-yn-3-one-(3Z)-oxime and 100 mL of 80% aqueous acetic acid (0.035 mol) of hydroxylammonium hydrochloride and 2.9 g (0.035 mol) of sodium acetate are added. The reaction mixture is stirred for about 50 h, and then purified as described in Example 4 to yield 8.5 g (85%) of the title compound, the pure E-oxime. Mp: 196-198° C.

Example 7 d-(17α)-13-Ethyl-17-hydroxy-18,19-dinorpregn-4-ene-20-yn-3-one-(3E)-oxime

Under nitrogen, to a vigorously stirred solution of 5 g (0.01 mol) of d-(17α)-13-ethyl-17(acetyloxy)-18,19-dinorpregn-4-ene-20-yn-3-one-(3Z)-oxime in 50 mL of methanol, 1.7 g (0.04 mol) of lithium hydroxide monohydrate is added at 0-5° C. and stirring is continued for another 2 h. After the reaction is complete (as checked by thin layer chromatography), the reaction mixture is poured into 500 mL of water and the pH of the obtained suspension is adjusted to 7.5-9 with acetic acid. The precipitated product is filtered off, washed with water until neutral, and then dried below 60° C. in vacuum. The obtained crude product (4.5 g) is recrystallized from acetonitrile to yield 4 g (90.2%) of d-(17α)-13-ethyl-17-hydroxy-18,19-dinorpregn-4-ene-20-yn-3-one-(3Z)-oxime. mp: 203-204° C.

d-(17α)-13-Ethyl-17-hydroxy-18,19-dinorpregn-4-ene-20-yn-3-one-(3E)-oxime is prepared according to the method described above from 5 g of d-(17α)-13-ethyl-17-(acetyloxy)-18,19-dinorpregn-4-ene-20-yn-3-one-(3E)-oxime. Yield: 4.1 g (92.45%); mp: 198-200° C.

Example 8 d-(17α)-13-Ethyl-17-hydroxy-18,19-dinorpregn-4-ene-20-yn-3-one-(3E)-oxime

Under nitrogen, to a vigorously stirred suspension of 1.25 g (0.017 mol) of hydroxylammonium hydrochloride and 1.45 g (0.017 mol) of sodium acetate in 60 mL of 50% aqueous acetic acid 2.5 g (0.008 mol) of d-norgestrel is added. After the reaction is complete (checked by thin layer chromatography), the reaction mixture is poured into 500 mL of water. The precipitated product is filtered off, washed successively with water, 5% aqueous ammonium hydroxide solution, and water until neutral, and then dried below 60° C. The crude product is recrystallized from dichloromethane to yield 2.27 g (86.7%) of the title compound. Mp.: 198-200° C.

Example 9 d-(17α)-13-Ethyl-17-hydroxy-18,19-dinorpregn-4-ene-20-yn-3-one-oxime (Mixture of Isomers)

To a vigorously stirred suspension of 5.8 g (0.07 mol) of sodium acetate in 80 mL of glacial acetic acid, 5 g (0.07 mol) of hydroxylammonium hydrochloride in 22 mL of water is added. Then 10 g (0.032 mol) of d-norgestrel is added to the reaction mixture under nitrogen and stirring is continued until the reaction is complete (as checked by thin layer chromatography). The reaction mixture is poured into 800 mL of water. The precipitated product is filtered off, washed successively with water, 5% aqueous ammonium hydroxide solution, and water until neutral, and then dried below 60° C. to yield 8.9 g (84.92%) of the title compound as a 55.8/44.2 mixture of E/Z-isomers. Mp.: 110-130° C.

Example 10

Pharmaceutical Composition Containing d-(17α)-13-ethyl-17-hydroxy-18,19-dinorpregn-4-ene-20-yn-3-one-(3Z)-oxime and Ethinyl Estradiol as Active Ingredients in Tablet Form 250 mg of Z-isomer of norelgestromin and 35 mg of ethinyl estradiol is mixed homogeneously with 75.715 g of lactose, 22.5 g of microcrystalline cellulose, 1 g of colloid silicon dioxide AEROSIL® (Evonik Degussa GmbH Ltd., Hanau, Del.) and 500 mg of magnesium stearate. The obtained powder mixture is compressed into tablets of 100 mg without granulation. About 1000 tablets are obtained.

Example 11

Pharmaceutical Composition Containing d-(17α)-13-ethyl-17-hydrox-y-18,19-dinorpregn-4-ene-20-yn-3-one-(3Z)-oxime and Ethinyl Estradiol as Active Ingredients in Tablet Form 250 mg of Z-isomer of norelgestromin and 35 mg of ethinyl estradiol are dissolved in 10 mL of ethanol and the so obtained mixture is sprayed on a homogeneous mixture of 75.715 g of lactose dried 20.5 g of cornstarch. Ethanol is removed from the mixture by fluidization drying. The obtained powder mixture containing the active ingredients is granulated with an aqueous solution of 2 g of polyvinylpyrrolidone (PVP) in fluidization equipment, and then dried. 1 g of colloid silicon dioxide and 0.5 g of magnesium stearate are homogenized with the granulated material. The granulated material is compressed into tablets of 100 mg. About 1000 tablets are obtained.

Example 12

Pharmaceutical Composition Containing d-(17α)-13-ethyl-17-hydroxy-18,19-dinorpregn-4-ene-20-yn-3-one-(3Z)-oxime and Ethinyl Estradiol as Active Ingredients in Tablet Form 250 mg of Z-isomer of norelgestromin, 35 mg of ethinyl estradiol and 2 g of polyvinylpyrrolidone (PVP) are dissolved in 10 mL of ethanol, and the so obtained mixture is sprayed on a homogeneous mixture of 75.715 g of lactose and 20.5 g of cornstarch in a high shear mixer. The mixture is granulated, and the ethanol is removed in a microwave vacuum drier. 1 g of colloid silicon dioxide and 0.5 g of magnesium stearate are homogenated to the granulated material. The granulated material is compressed into tablets of 100 mg. About 1000 tablets are obtained.

Example 13

Pharmaceutical Composition Containing d-(17α)-13-ethyl-17-hydroxy-18,19-dinorpregn-4-ene-20-yn-3-one-(3E)-oxime and Ethinyl Estradiol as Active Ingredients in Transdermal Patch Form A one-piece, matrix-type transdermal patch of 3 layers containing 6.0 mg of E-isomer of norelgestromin and 0.75 mg of ethinyl estradiol is prepared as follows.

For every patch unit 6.0 mg of E-isomer of norelgestromin, 0.75 mg of ethinyl estradiol, 25 mg of polyvinylpyrrolidone, 20 mg of lauryl lactate (absorption promoting agent) and 248 mg of polyisobutylene are dispersed in a 8:1:1 mixture of hexane/ethyl acetate/ethanol at room temperature for 45 min. The so obtained dispersion is poured onto the external membrane of the patch and dried at 70° C. for about 45 min. A protective membrane is layered on the surface of the dried matrix.

Example 14

Pharmaceutical Composition Containing d-(17α)-13-ethyl-17-hydroxy-18,19-dinorpregn-4ene-20-yn-3-one-(3E)-oxime and Ethinyl Estradiol as Active Ingredients in Transdermal Gatch Form A one-piece, matrix-type transdermal patch of 3 layers containing 6.0 mg of E-isomer of norelgestromin and 0.75 mg of ethinyl estradiol is prepared as follows.

For every patch unit, 261 mg of polydimethylsiloxane and 17 mg of polyvinylpyrrolidone is homogenated at room temperature. 15 mg of methyl laureate, 6.0 mg of E-isomer of norelgestromin and 0.75 mg of ethinyl estradiol are added to the mixture, and it is dispersed with 350 mL of ethanol at room temperature for 45 min. The so obtained dispersion is poured onto the external membrane of the patch and dried at 70° C. for about 45 min. A protective membrane is layered on the surface of the dried matrix.

Example 15

Determination of Physicochemical Parameters of Isomers

According to the relative orientation of the hydroxyl group of the oxime group of norelgestromin, there are two geometric isomers of the compound. These isomers can be separated by column chromatography. As determined herein, the Z isomer is more polar than the E isomer. For isomers that differ in polarity, absorption through the skin may also differ. This issue is relevant to, e.g., the application of isomeric mixtures of norelgestromin in transdermal patches. This issue was investigated. The investigations included the physico-chemical properties of the pure isomers as well as their in vitro pharmacokinetic study. During the physicochemical study, the water solubility of the individual norelgestromin isomers was determined, as well as their lipophilicity by traditional and isocratical HPLC.

Protocol for Solubility Measurement

The determination of equilibrium solubility of E and Z isomers of norelgestromin was carried out in distilled water. 20 mg of norelgestromin was added to 20 mL of distilled water at room temperature. The suspension was stirred continuously and samples were withdrawn from time to time. The samples were filtered, and the norelgestromin content of the filtrates was determined by a spectrophotometrical method measuring UV absorption. The spectrophotometrical measurements were performed on a VARIAN Cary 3E spectrophotometer at room temperature.

Protocol for Lipophilicity Measurement

Lipophilicity was determined by an HPLC method. The HPLC measurements were performed on a Thermo Separation Product (SpectraSystem P4000 and SpectraFOCUS Forward Optical Scanning Detector) HPLC instrument. Data were analyzed by ChromQuest (ver. 2.51) software.

For reversed-phase HPLC measurements, a Nova-Pak C18 column was used (dimension of 4 μm×4.6 mm×250 mm: Waters, Ireland). Detection was performed at λ=280 nm and 25° C. The flow rate of the mobile phase was 1.0 mL/min. HPLC gradient grade acetonitrile was used as organic component (Merck KGaA., Darmstadt, Germany). The retention data of the two isomers were obtained by isocratical analysis of the mobile phases containing different amounts of acetonitrile. The void time ($t_0$) was determined by injection of methanol.

Samples were dissolved in a 1:1 mixture of acetonitrile: water in a concentration of 1 mg/4 mL. The log k' values were calculated from the mean retention time measured after two subsequent injections of 10 μL volume (log k'=log((tR−$t_0$)/$t_0$)). The log k' values were represented as a function of the concentration of acetonitrile. The void time ($t_0$) was found to be 1.49 min in this experimental arrangement.

The chromatographical hydrophobicity index (CHI) is a measure of the lipophilic character of the compounds in the reversed phase HPLC measurements. By definition, the CHI parameter is that concentration of acetonitrile of the mobile phase where log k'=0.

TABLE 1

| Parameter | E-isomer | Z-isomer |
| --- | --- | --- |
| Water solubility | 3.8 μg/mL | 12.1 μg/mL |
| Polarity (k', HPLC) | 1.02 | 1.46 |
| Polarity (CHI index, HPLC) | 74 | 70 |

Example 16

Determination of Metabolic and Distribution Parameters of Isomers of Norelgestromin The in vitro pharmacokinetic study included the metabolic stability, the metabolic clearance, and the Caco-2 permeability of the compounds.

Protocol for Assessment of Metabolic Stability and Clearance

The metabolic stability of norelgestromin E and Z isomers was examined in human liver microsomes. The 2.5 mL incubation mixture contained 6 mM of Na-pyrophosphate, 5 mM of $MgCl_2$, 5 mM of glucose-6-phosphate, 1 U/mL of glucose 6-phosphate dehydrogenase, human liver microsomes (1 mg/mL) and 5 μM of norelgestromin E or Z isomers. The pH was adjusted with 100 mM of Tris-HCl buffer to pH 7.4. The reaction was started by the addition of 5 mM of NADPH. 0.5 mL samples were taken at 0.5 and 20 minutes with immediate precipitation by 0.5 mL of ice-cold methanol. 1 mL precipitated samples were centrifuged for 30 min at 1200 g, and 10 μL of supernatant was injected into the HPLC.

Analytical measurements were conducted using a Merck-Hitachi HPLC system, with UV monitoring at 244 nm. Unchanged material was measured and intrinsic clearance ($Cl_{int}$) and metabolic bioavailability (F%) was calculated with the following equations:

$$dc/dt/c_0 = Cl_{int}, \text{(mL/min×g protein)},$$

where dc/dt is the concentration change in a given period of time and $c_0$ is the initial concentration of the norelgestromin isomer (measured in the 0 min sample). Additionally, $$Cl_{int1} \times 45 = Cl_{int2} \text{ (mL/min×g liver) and } EH = Cl_{int2}/Cl_{int2} + HBF,$$

where EH is hepatic extraction and HBF is the hepatic blood flow. Finally the metabolic stability:

$$F\% = (100 - EH) \times 100$$

For statistical analysis, Student's t-test was used (Microsoft Excel). The results summarized in Table 2 are calculated as a mean of 3 parallel measurements.

Protocol for Caco-2 Permeability Measurement

Drug absorption studies were performed with Caco-2 human adenocarcinoma (epithelial) cell line monolayers as an in vitro model. Passive flux characteristics of drugs across the Caco-2 monolayer have shown a correlation with human oral bioavailability.

Caco-2 cells obtained from American Type Culture collection, Rockville, Md., (ATCC) were grown at 37° C. in an atmosphere of 5% $CO_2$ in Dulbecco's modified eagle medium supplemented with 10% heat inactivated fetal bovine serum (GIBCOBRL 11360-039) and antibiotics: penicillin 100 U/mL, and streptomycin 100 μg/mL (GIBCOBRL 15140-031).

Confluent cell monolayers grown in an incubator (at 37° C. with 5% $CO_2$/95% $O_2$ and 95% humidity) were subcultured every seven days by treatment with 0.25% trypsin containing 1 mM EDTA.

19-23-day-old confluent monolayers of fully differentiated Caco-2 cells were used for transport studies after 6-10 passages.

EHS Cell Attachment Matrix (Promega G5971), Minimum Essential medium Eagle (MEM) with Earle salts, L-Glutamine (GIBCOBRL 41500-091) and Transwell Polycarbonate Membrane (Costar 3401) were used.

Coated Transwells with EHS Cell Attachment Matrix (Promega G5971) and 200000-500000 Caco-2 cells are applied/inserted. Caco-2 monolayers were grown on the luminal side/apical compartment of transwells.

The E- and Z-isomers of norelgestromin were assayed at 50 μM concentration. [$^{14}$C]-Mannit was used as paracellular marker ($3.7 \times 10^4$ Bq/test chamber).

After removal of cell culture medium, three parallel Caco-2 cell monolayers were preincubated for each test compound with prewarmed (37° C.) HBBS-TRIS (400 μL to the luminal side and 1.5 mL to the basolateral side/compartment) for 20 min at 37° C.

The medium was changed, followed by addition of 0.4 mL 50-100 gM working concentration of investigated and reference molecules to the luminal/apical compartment of inserts.

Measurement of absorption (luminal side to basolateral side) was made by obtaining samples from the luminal/apical ("donor") compartment at zero time point and from the basolateral ("receiver" side) at every 15 min (3×).

The concentrations of the isomers were determined by liquid chromatography with ultraviolet (HPLC/UV) analysis. Method: gradient elution at 35° C. Eluent A: methanol—0.05 M, ammonium acetate=300-200+500 μL 10% acetic acid. Eluent B: methanol. Flow: 0.50 mL/min. Detection: 240 nm. Column type: Merck Purospher C-18.

Dim.: 125–3 mm.+guard. Chrom Type: HPLC Channel:2. Peak quantitation: height; calculation method: EXT-STD.

The albuminal concentrations of the penetrated isomers are shown in Table 2.

TABLE 2

| Parameter | E-isomer | Z-isomer |
| --- | --- | --- |
| Metabolic stability | 86.7 ± 1.67 | 91.9 ± 1.52 |
| Metabolic clearance (mL/min g liver) | 0.1815 ± 0.026 | 0.1042 ± 0.021 |
| Concentration on the abluminal side (μM in the 30$^{th}$ min) | 1.27 ± 0.56 | 1.98 ± 0.78 |

As the above data show, the Z-isomer of norelgestromin is more soluble in water than the E-isomer. In the case of the Z-isomer, the penetration across the epithelial cell layer is faster, the metabolic stability is higher, and the clearance is lower than in the case of the E-isomer. These properties show that, after oral administration, the absorption of the Z-isomer is expected to be better than that of the E-isomer. Therefore, use of the Z-isomer in orally administered formulations (for example in tablets) is more advantageous.

Example 17

Siddiqui, et al., *J. Pharm. Biopharm.*, 17:405 (1989), have shown by carrying out experiments on isolated human skin preparations that the lipophilic steroids penetrate faster across the human epidermis than the polar steroids, but the rate of clearance is about the same in both cases. According to the experiments of solubility and polarity provided herein, the E-isomer of norelgestromin is significantly more lipophilic than the Z-isomer. According to the experiments of Siddiqui and coworkers, the penetration of the more lipophilic E-isomer is faster across the epidermis than that of the Z-isomer. Therefore the application of E-isomer in transdermal patches is more advantageous.

The beneficial effect of the increasing lipophilicity for the transdermal absorption was proven by carrying out a structure-absorption experiment with six different steroids. In the following publications: *Int. J. Pharm.* 217:1 (2001), and *J. Chromatography* 49:631 (1993), it has been shown that the chromatographical hydrophobicity index (CHI) measured under isocratical conditions is a reliable descriptor of lipophilicity. The CHI values of the investigated steroids were determined according to these experiments (Table 3) and correlated with the measured stratum corneum/water distribution coefficients.

TABLE 3

| Steroid compound | CHI | Log Kp |
| --- | --- | --- |
| Hydrocortisone | 33.8 | −9.08 |
| Estriol | 40.45 | −7.95 |
| Cortexolone | 54.87 | −7.68 |
| Estradiol | 65.19 | −7.08 |
| Testosterone | 75.87 | −6.95 |
| Pregnenolone | 95.36 | −6.38 |

The obtained good correlation ($r^2$=0.88) shows that the steroid having a higher CHI index, i.e., is more lipophilic, penetrates better across the stratum corneum. FIG. 1 shows the correlation between measured and predicted log $K_p$ data (95% confidence intervals are indicated by dashed lines) for other steroids. According to our measurements, the CHI index of the E-isomer is higher than that of the Z-isomer. In a preferred embodiment, the substantially pure E-isomer of norelgestromin is formulated as a transdermal patch.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A process for preparing d-(17α)-13-ethyl-17-hydroxy-18,19-dinorpregn-4-ene-20-yn-3-one-(3E)-oxime comprising converting d-norgestrel into a mixture of norelgestromin isomers; and adding to the reaction mixture about 10 to about 25 volume percent of water; and stirring the resulting mixture for at least 24 hours.

2. The process according to claim 1, wherein said d-norgestrel is reacted with hydroxylammonium acetate in a ratio of about 1.2 mol to about 5 mol per mole of said d-norgestrel, in acetic acid containing not more than 50 mass percent of water; at a temperature of about 15° C. to about 50° C.; and stirred for about 15 minutes to about 45 minutes.

3. The process according to claim 2, wherein said reaction mixture is stirred for about 24 to about 72 hours after the addition of water.

4. The process according to claim 1, wherein d-norgestrel is reacted with a hydroxylammonium salt in a ratio of about 1.2 to about 5 mol per mole of d-norgestrel, and with an alkali metal acetate in a ratio of not more than 1 mole per mole of said hydroxylammonium salt; in acetic acid containing not more than 50 mass percent of water; at a temperature of about 15° C. to about 50° C.; and stirred for about 15 minutes to about 45 minutes.

5. The process according to claim 4, wherein said reaction mixture is stirred for about 24 to about 72 hours after the addition of water.

6. The process according to claim 2, wherein the reaction mixture of d-norgestrel is stirred at temperature of about 10° C. to about 30° C.

7. The process according to claim 6, further comprising isolating the E-norelgestromin from the reaction mixture; and recrystallizing the isolated E-norelgestromin.

8. A process of preparing d-(17α)-13-ethyl-17-hydroxy-18,19-dinorpregn-4-ene-20-yn-3-one-(3Z)-oxime comprising converting d-norgestrel into a mixture of norelgestromin isomers; adding about 10-fold volume of water after the reaction is complete; and the precipitated isomeric mixture is isolated and stirred in dichloromethane.

9. The process according to claim 8, wherein said d-norgestrel is reacted with hydroxylammonium acetate in a ratio of about 1.2 mol to about 5 mol per mole of said d-norgestrel, in acetic acid containing not more than 50 mass percent of water; at a temperature of about 15° C. to about 50° C.; and stirred for about 15 minutes to about 45 minutes.

10. The process according to claim 8, wherein said d-norgestrel is reacted with a hydroxylammonium salt in a ratio of about 1.2 to about 5 mol per mole of d-norgestrel, and with an alkali metal acetate in a ratio of not more than 1 mole per mole of said hydroxylammonium salt; in acetic acid containing not more than 50 mass percent of water; at a temperature of about 15° C. to about 50° C.; and stirred for about 15 minutes to about 45 minutes.

11. The process according to claim 8, further comprising filtering the insoluble (3E)-oxime norelgestromin isomer; and purifying the (3Z)-oxime by column chromatography.

12. The process according to claim 11, further comprising recrystallizing the Z-norelgestromin.

13. A process of preparing d-(17α)-13-ethyl-17-hydroxy-18,19-dinorpregn-4-ene-20-yn-3-one-(3E)-oxime comprising converting d-norgestrel into a mixture of norelgestromin isomers; adding about 10-fold volume of water after the reaction is complete; and the precipitated isomeric mixture is isolated and stirred in dichloromethane.

14. The process according to claim 13, wherein said d-norgestrel is reacted with hydroxylammonium acetate in a ratio of about 1.2 mol to about 5 mol per mole of said d-norgestrel, in acetic acid containing not more than 50 mass percent of water; at a temperature of about 15° C. to about 50° C.; and stirred for about 15 minutes to about 45 minutes.

15. The process according to claim 13, wherein said d-norgestrel is reacted with a hydroxylammonium salt in a ratio of about 1.2 to about 5 mol per mole of d-norgestrel, and with an alkali metal acetate in a ratio of not more than 1 mole per mole of said hydroxylammonium salt; in acetic acid containing not more than 50 mass percent of water; at a temperature of about 15° C. to about 50° C.; and stirred for about 15 minutes to about 45 minutes.

16. The process according to claim 13, further comprising filtering the insoluble (3E)-oxime norelgestromin isomer; and purifying the (3E)-oxime by column chromatography.

17. The process according to claim 13, further comprising recrystallizing the E-norelgestromin.

18. A process of preparing d-(17α)-13-ethyl-17-hydroxy-18,19-dinorpregn-4-ene-20-yn-3-one-(3Z)-oxime comprising stirring a mixture of E/Z isomers of norelgestromin in dichloromethane; filtering the insoluble (3E)-oxime isomer; and purifying the filtrate to give the (3Z)-oxime of norelgestromin.

19. The process according to claim 18, wherein purifying the filtrate comprises column chromatography using silica gel as adsorbent and a mixture of apolar-polar solvents as eluent.

20. The process according to claim 18, further comprising recrystallizing the Z-norelgestromin.

* * * * *